(12) United States Patent
Vodanoy et al.

(10) Patent No.: US 7,807,042 B2
(45) Date of Patent: Oct. 5, 2010

(54) SYSTEM FOR AND METHOD OF PATCH CLAMP ANALYSIS

(75) Inventors: Vitaly J. Vodanoy, Auburn, AL (US); Solomon Yilma, Iowa City, IA (US); Charles D. Ellis, Auburn, AL (US); Bogdan M. Wilamowski, Auburn, AL (US); Thomas Hasling, Columbus, GA (US)

(73) Assignee: Auburn University, Auburn, AL (US)

( * ) Notice: Subject to any disclaimer, the term of this patent is extended or adjusted under 35 U.S.C. 154(b) by 981 days.

(21) Appl. No.: 11/341,160

(22) Filed: Jan. 27, 2006

(65) Prior Publication Data

US 2006/0166185 A1      Jul. 27, 2006

Related U.S. Application Data

(60) Provisional application No. 60/647,649, filed on Jan. 27, 2005.

(51) Int. Cl.
*G01N 33/487* (2006.01)

(52) U.S. Cl. .............. 205/777.5; 204/403.01; 435/173.4

(58) Field of Classification Search ........... 204/403.01; 205/777.5; 435/173.4
See application file for complete search history.

(56) References Cited

U.S. PATENT DOCUMENTS

| | | | |
|---|---|---|---|
| 4,006,063 A * | 2/1977 | Ensanian | 205/791.5 |
| 4,294,091 A | 10/1981 | Prunbauer | 70/276 |
| 5,774,223 A | 6/1998 | Urakami et al. | 356/394 |
| 6,288,527 B1 | 9/2001 | Sugihara et al. | 324/71.1 |
| 6,350,762 B1 * | 2/2002 | Niwa et al. | 514/334 |
| 6,488,829 B1 * | 12/2002 | Schroeder et al. | 204/403.01 |
| 6,788,071 B2 | 9/2004 | Vodyanoy et al. | 324/603 |
| 2002/0006357 A1 * | 1/2002 | McGeoch et al. | 422/82.01 |
| 2003/0020489 A1 * | 1/2003 | Vodyanoy et al. | 324/603 |
| 2003/0052002 A1 * | 3/2003 | Vogel et al. | 204/403.01 |
| 2004/0146849 A1 | 7/2004 | Huang et al. | 435/4 |

FOREIGN PATENT DOCUMENTS

JP           62063823 A           3/1987

OTHER PUBLICATIONS

Yuri E. Korchev et al., Cell Volume Measurement Using Scanning Ion Conductance Microscopy, Jan. 2000, p. 451-457, Biophysical Journal, vol. 78.
Vitaly Vodyanoy, Olfactory Sensor, 1988, IEEE Engineering in Medicine & Biology Society 10th Annual International Conference.
O.P. Hamill et al., Improved Patch Clamp Techniques for High-Resolution Current Recording From Cells and Cell-Free Membrane Patches, 1981, p. 85-100, Pflugers Archiv European Journal of Physiology.

* cited by examiner

*Primary Examiner*—Kaj K Olsen
(74) *Attorney, Agent, or Firm*—Haverstock & Owens LLP

(57) ABSTRACT

A system and method for automated patch clamp analysis of biological tissue such as cellular membrane. A biological membrane is applied to a porous semiconductor substrate, and laser energy is imparted thereon. Voltage clamped electrodes detect current across the membrane to indicate ion channel activity.

12 Claims, 4 Drawing Sheets

SYSTEM FOR AND METHOD OF PATCH CLAMP ANALYSIS

RELATED APPLICATION(S)

This Patent Application claims priority under 35 U.S.C. §19(e) of the co-pending,co-owned U.S. Provisional Patent Application, Ser. No. 60/647,649, filed Jan. 27, 2005, and entitled "SYSTEM AND METHOD FOR PATCH CLAMP ANALYSIS." The Provisional Patent Application, Ser. No. 60/647,649, filed Jan. 27, 2005, and entitled "SYSTEM FOR AND METHOD OF PATCH CLAMP ANALYSIS" is also hereby incorporated by reference in its entirety.

FIELD OF THE INVENTION

The present invention relates generally to the analysis of cell characteristics and behavior. More specifically, the present invention relates to an improved method of carrying out patch clamp analysis, and a system and apparatus for practicing that method.

BACKGROUND OF THE INVENTION

The patch clamp technique (Hamill, Neher, Sakmann and Sigworth, *Improved Patch Clamp Techniques for High-Resolution Current Recording from Cells and Cell-Free Membrane Patches*, PFLUGERS ARCH. 391, 85-100, 1981) is used in the study of physiology, particularly in the study of behavior of ion channels and macroscopic currents in cells. The technique allows voltage clamped measurement of ionic current in either a small patch of cell membrane, or the entire membrane area of a small cell. Patch clamp studies are commonly used to facilitate drug screening in the pharmaceutical industry, particularly in drugs that act by blocking or regulating channel activity to and from cells, to directly assay the function of genes that encode ion channel and transporter proteins, and in neuroscience research, as well as various other applications.

In conventional patch clamp recording, a glass or fused-quartz micropipette having a tip opening on the order of 1 micron (1 μm) in diameter is gently applied to form a seal against a cell membrane, isolating a patch of the membrane with a seal resistance on the order of 1-100 GΩ. The micropipette is typically filled with saline solution, and acts as an electrode to permit detection and recording of ion channel current through the membrane, as well as observation and recording of the opening and closing of ion channels in the membrane.

Known methods of patch clamp recording, however, typically require a high degree of technical proficiency, and are quite time consuming and expensive. For example, the micropipette generally must be manually manipulated with extreme precision to contact and seal against a target cell under observation. And because known patch clamp methods analyze only a single cell or a patch of a cell's membrane surface, multiple patch clamp analyses typically must be carried out for statistical confirmation of the observations. But extreme difficulty in exactly replicating the study conditions over multiple procedures can drastically increase the expense and time required to complete a study, and add to the uncertainty of the observed results.

The application of a voltage across a biological or synthetic membrane can be utilized in a variety of applications. For example, application of a localized voltage across a membrane can be used to address or map biological structures such as ion channels and/or to detect binding events at a channel.

The presence or absence of such ion channels or carriers in a membrane can act as a molecular switching element that converts a binding event into an electrical signal, functioning as a transducer in a biosensor or nanodevice. For example, in a membrane in which a molecular channel or switch is held open when a specific analyte is bound, ion transport through the membrane is permitted when the analyte is bound, but is blocked when the analyte is not bound. If a voltage is applied across the membrane, a current pulse will be observed if ion transport occurs through the membrane, indicating an open channel and thus the presence of a binding event. Conversely, if a voltage is applied across the membrane and no current is observed (e.g., no ion transport through the membrane), a closed channel (and thus the absence of a binding event) is indicated.

The very small scale of the membranes and the molecules forming ion channel and ion carrier molecular switches under investigation (commonly on the order of about 100 Angstroms), as well as the relatively high density of ion channels on a substrate renders the addressing of these channels very difficult using known techniques. One conventional solution for the addressing of biological structures such as ion channels would be to make electrical connections to all or to many of these molecular switches. The applied voltage and responses of individual addresses on a substrate such as a silicon wafer surface could be scanned with the aid of computerized circuitry. However, the resolution of known addressable electrodes is poor, and manufacturing of an electrode system on the substrate surface would likely prove difficult and expensive. Also, voltage applied to a membrane in an electrolytic solution is typically conducted through the electrolyte along the membrane surface, rendering it difficult or impossible to address or map a specific location on the membrane.

Thus, it can be seen that needs exist for improved methods of and apparatus for patch clamp analysis. It is to the provision of improved apparatus and methods meeting this and other needs that the present invention is primarily directed.

SUMMARY OF THE INVENTION

In one aspect, a method of patch clamp analysis of a biological membrane, comprises applying the biological membrane to a semiconductive substrate having at least one channel extending therethrough, placing a first electrode in conductive contact with a first side of the biological membrane and a second electrode in conductive contact with a second side of the biological membrane and detecting a current between the first electrode and the second electrode. Detecting a current between the first electrode and the second electrode comprises measuring ion current to detect activity of at least one ion channel through the biological membrane. The method further comprises directing laser energy toward a portion of the semiconductive substrate. The laser energy is applied by scanning a beam along a controlled path across the biological membrane. The method further comprises clamping the voltage between the first electrode and the second electrode.

In another aspect, a system for patch clamp analysis of a biological membrane, comprises a porous semiconductor substrate for receiving the biological membrane thereon, a first electrode for conductive contact with a first side of the membrane, a second electrode for conductive contact with a second side of the membrane, a voltage clamp between the first and second electrodes and a laser light source for directing a beam toward a portion of the semiconductor substrate. The first electrode and the second electrode are incorporated on an integrated electronic component. The voltage clamp is also incorporated on the integrated electronic component. The integrated electronic component further comprises at least one onboard amplifier.

In yet another aspect, an integrated electronic component comprises at least one island of semiconductor substrate for receiving a biological membrane thereon, and first and second electrodes in connection with each island of semiconductor substrate. The integrated electronic component further comprises voltage clamp circuitry. The integrated electronic component further comprises at least one onboard amplifier.

In another aspect, a method for fabricating a patch clamp device, comprises depositing a silicon dioxide on a wafer, etching a hole in an oxide, oxidizing the wafer and electroplating the wafer with copper until the hole is almost closed.

In another aspect, an automated system for patch clamp analysis, comprises a carrier for membrane under analysis, a source of laser energy and a controller for controlling scanning of the source of laser energy across a membrane on the carrier.

In yet another aspect, a method of patch clamp analysis of a cellular membrane, the method comprises depositing the cellular membrane on a semiconductive substrate having at least one channel extending therethrough, applying a solid electrolyte to the semiconductive substrate to contact the cellular membrane, applying an electrolytic solution over the cellular membrane, applying suction through one or more pores to the cellular membrane to ensure a seal is formed around the one or more pores, placing a first electrode in conductive contact with a first side of the cellular membrane, and a second electrode in conductive contact with a second side of the cellular membrane and detecting a current between the first electrode and the second electrode. Applying suction to the cellular membrane to ensure a seal is formed further comprises breaking the cellular membrane and providing electrically conductive communication between the cell interior and the electrolytic solution. The solid electrolyte is a composition made from biopolymer and selected from a group consisting of K, Na, and Cl ions. The electrolytic solution includes about 125 mM NaCl, about 5 mM KCl, about 1.25 mM $NaH_2PO_4$ and about 5mM Tris (pH 7.4). Detecting a current between the first electrode and the second electrode comprises measuring ion current to detect activity of at least one ion channel through the cellular membrane. The method further comprises directing laser energy toward a portion of the semiconductive substrate. The laser energy is applied by scanning a beam along a controlled path across the cellular membrane. The method further comprises clamping the voltage between the first electrode and the second electrode.

DETAILED DESCRIPTION OF THE PREFERRED EMBODIMENT

The present invention provides improved methods and systems for patch clamp analysis. In example embodiments, the methods and systems of the present invention will permit a practitioner to obtain patch clamp study results in a considerably faster and less expensive manner than would be possible using many previously known techniques. Example forms of the invention facilitate simultaneous patch clamp analysis of multiple samples on a single substrate, reducing the difficulty commonly encountered in replicating test conditions over multiple independent samples.

In example form, a membrane to be studied is grown on a porous semiconductor substrate, for example as described in U.S. Pat. No. 6,788,071 to Vodyanoy et al. which is hereby incorporated by reference for all purposes. The membrane is effectively sealed against the substrate around each pore, and the pores of the substrate thereby form an array of channel electrodes each of which can function in similar manner to the micropipette channel electrode of a traditional patch clamp setup. A positionally-controlled narrow-beam light source can be scanned across the array to selectively open and close ion channels of the membrane under observation and induce ion current flow.

Figure 1:
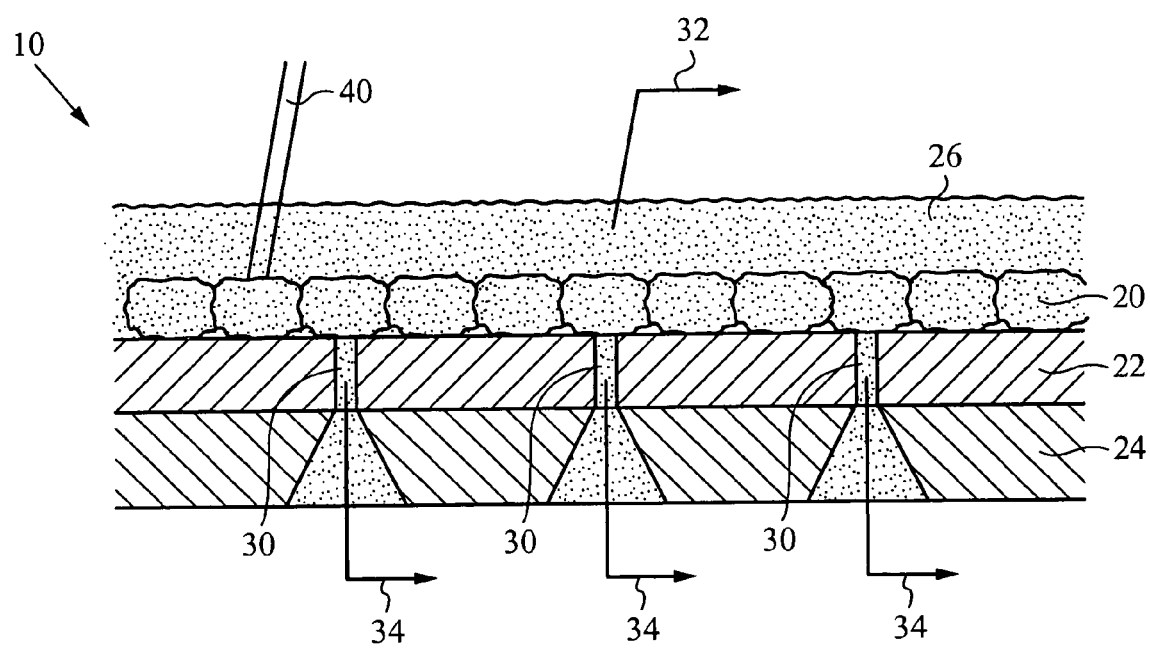
FIG. 1 shows a cross-sectional view of a patch clamp system for analyzing a membrane according to an example form of the present invention.

An example embodiment of a system 10 for carrying out a method of patch clamp analysis according to the present invention is shown in FIG. 1. A cellular membrane 20 is preferably deposited on a porous semiconductor substrate 22 such as a silicon wafer. A solid electrolyte 24 is preferably applied to a first or lower side of the semiconductor substrate such that the solid electrolyte is in contact with the lower part of the cell, and an electrolytic solution 26 is preferably applied over the membrane. An exemplary substrate includes an n-type semiconductor plate of about 100 microns thick covered with about 1 micron porous silicon film with pores of about 0.5 microns in diameter. An exemplary solid electrolyte includes a composition made of a biopolymer and K, Na and Cl ions. A typical liquid electrolyte includes about 125 mM NaCl, 5mM KCl, 1.25 mM $NaH_2PO_4$ and 5mM Tris (pH 7.4). A plurality of nano- or micro-scale channels or pores 30 preferably extend through the substrate, into communication with the cell membrane of individual cells of the cellular membrane 20. Suction is applied to the cell membranes through the pores 30 to ensure a seal is formed around the pores, and optionally to break the cell membrane and provide electrically conductive communication between the cell interior and the electrolytic fluid in the pores.

Suction is preferably applied by applying a negative pressure from the first or lower side of the semiconductor substrate through the pores 30. Alternatively, suction is applied by applying a positive pressure from a second or upper side of the semiconductor substrate 22. When negative pressure is applied to the lower side, the pores 30 are preferably filled by a liquid electrolyte. One or more first electrodes 32 are preferably provided in electrically conductive communication with the electrolytic solution 26 on a first side of the membrane, and one or more second electrodes 34 are preferably provided in electrically conductive communication with the cell interior or second side of the membrane; and the voltage is clamped between the first and second electrodes 32, 34 such that the voltage is maintained constant at any new level (which can be at zero level) and current can be measured. If, for example, the voltage is clamped at a certain level and the resistance of the cellular membrane is constant, the current is constant. If, however, the membrane suddenly generates additional voltage, the system 10 immediately generates a current in a direction that compensates for this additional voltage, so as to keep the clamped voltage constant. This transient current is observed and recorded. A similar situation occurs when voltage is clamped and suddenly the resistance of the cellular membrane is changed. Here, again the system 10 sends a current that is proportional to the resistance change and maintains the voltage constant. In the case of the cellular membrane that covers pores 30, it is convenient to maintain voltage that compensates all ion imbalances in the system and keeps the total membrane current value close to zero.

A laser 40 or other energy source is preferably scanned across the membrane 20, from cell to cell, to open or close ion channels of the cells and induce or block ion current therethrough, which current is observed and recorded for analysis. The laser 40 introduces a local electrical charge imbalance (imbalance of electron density produced by a photo-electric effect in the semiconductor) that would have resulted in local change of voltage in the absence of clamped voltage applied to the ion channels. Because the voltage is clamped, the photo-induced electron imbalance results in a current through the ion channels, which is observed and recorded. Thus, the laser 40 provides an electrochemical gradient that drives ions through the channels. Channels can be opened and closed spontaneously, can be opened and closed by voltage, or can be controlled chemically by binding other molecules or ions. The nature of this local change of voltage is substantially as described in U.S. Pat. No. 6,788,071, incorporated herein by reference. The potential change is generated in the porous semiconductor close to the electrode 34. The voltage between the electrodes 32 and 34 is defined as the difference between electrical potentials of the electrodes 34 and 32. If the potential of the electrode 34 is changed by a photo-electric effect, the difference between the potentials of the electrodes 34 and 32 and the voltage between the electrodes is also changed. This voltage is applied locally to the area of the membrane 20 illuminated by the laser light. One or more pharmaceuticals or various other agents can be delivered to the cells of the membrane 20 to analyze their effect on ion channel activity and/or other cellular characteristics.

Figure 2:
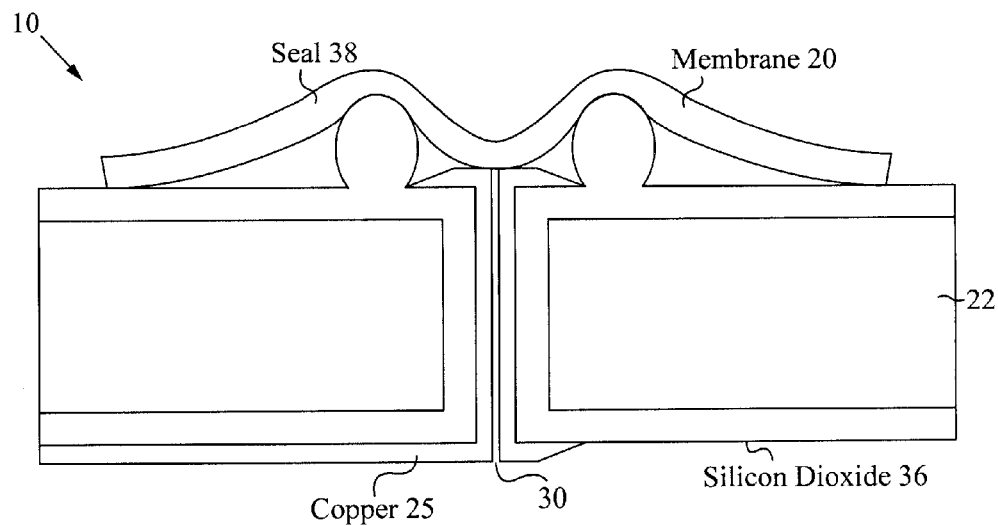
FIG. 2 shows a planar patch clamp system for analyzing a membrane in cross-sectional detail.

An exemplary method of fabricating a planar patch clamp structure 10 that has a high resistivity (G ohm) seal and low resistivity electrical contact to a cell membrane 20, is shown in greater detail in FIG. 2. A silicon substrate 22 (about 500 µm thick) with about 500 nm silicon dioxide is used as the semiconductor substrate. A reflowable silicon dioxide 36 is deposited and patterned on the silicon substrate 22 to form a seal ring 36. Holes or pores 30 on the order of about 10 µm are patterned and etched in the original oxide corresponding to the electrical contact areas. Pores 30 on the order of about 200 µm are deep reactive etched in the silicon substrate 22 using the oxide as a mask. The silicon substrate 22 or silicon wafer is oxidized to a thickness of about 1 µm to allow electrical isolation. The silicon wafer 22 is placed in an LPCVD furnace to deposit a thin conformal layer of tungsten in the holes 30 as a seed layer for subsequent copper electroplating. Copper 25 is electroplated until the about 10 µm pore 30 is almost closed to about 1 µm hole. The wafer 22 is background until the small hole is exposed. The backside of the wafer 22 is patterned and metalized to connect the electrical contact areas to peripheral connecting pads. This structure 10 allows electrical contact and the ability to pull a negative pressure on the cellular membrane 20, helping guarantee a seal and intimate contact with the membrane.

Figure 3:
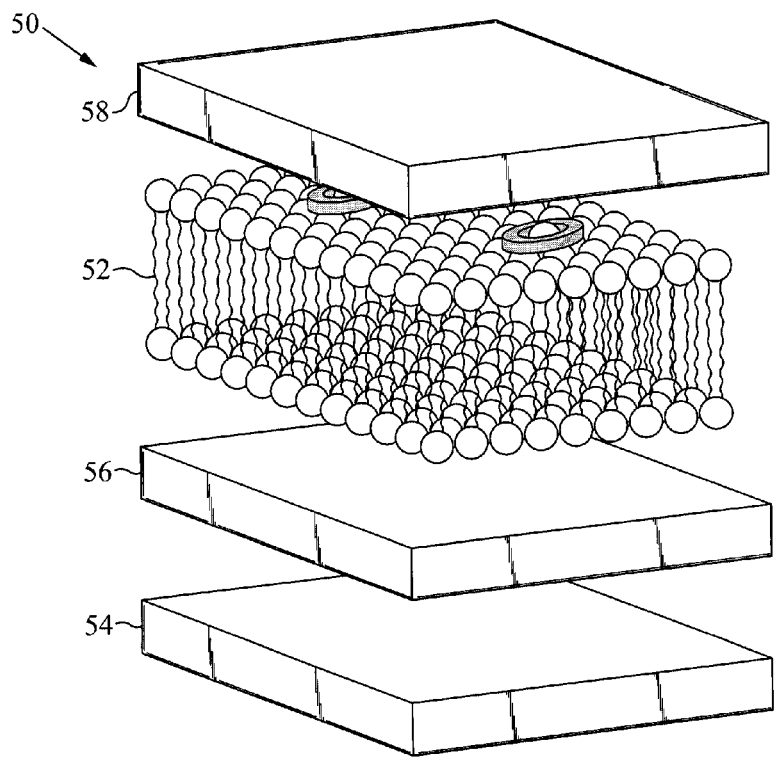
FIGS. 3, 4, and 5 show a planar patch clamp system according to the present invention being energized by a laser.
Figure 4:
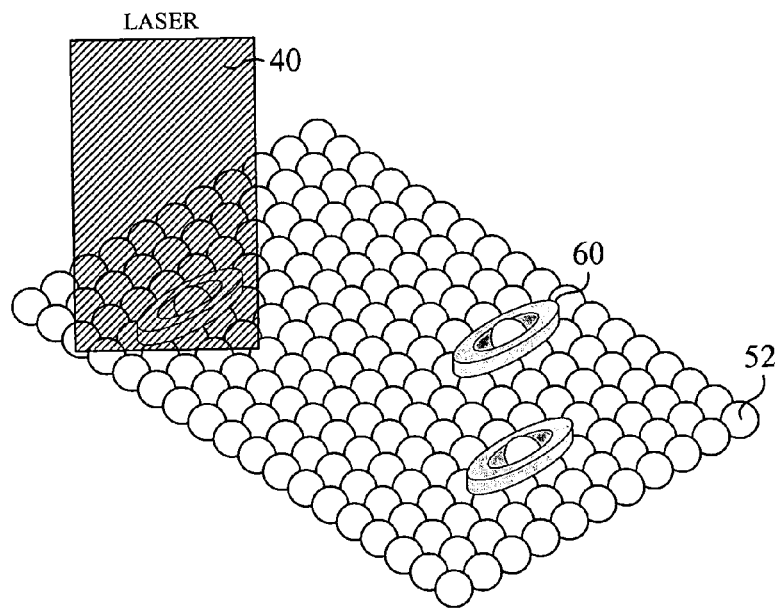
Figure 5:
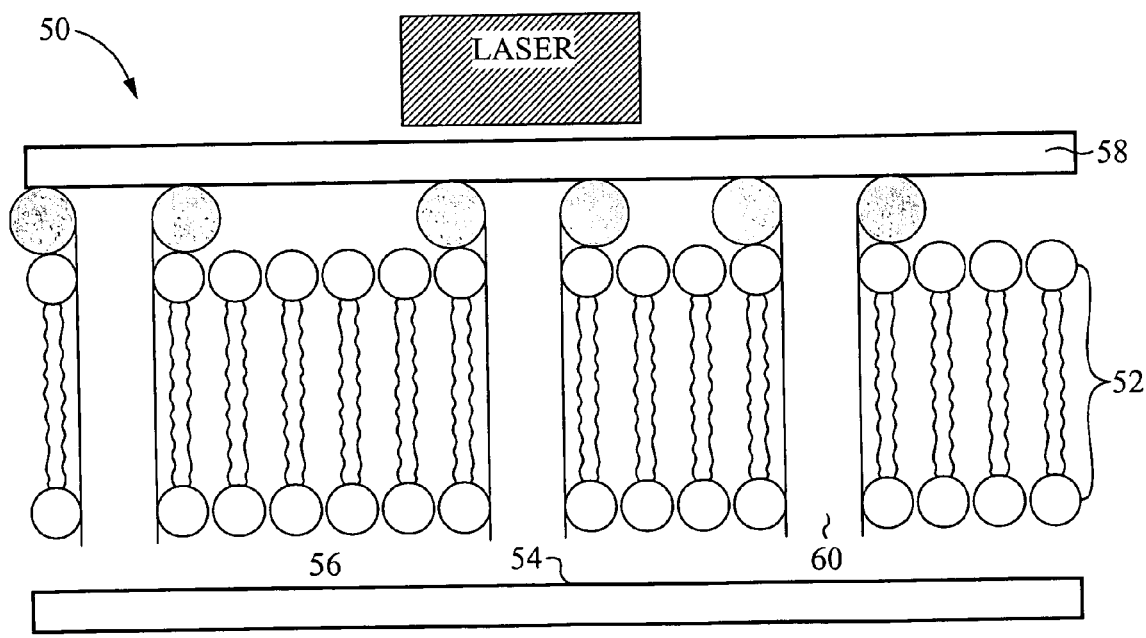

As seen more clearly in FIGS. 3-5, a biosensor 50 for use with a method of patch clamp analysis according to another example embodiment of the present invention is shown. A cellular membrane 52, such as a double lipid membrane, is preferably deposited on a porous semiconductor substrate 54 such as a silicon wafer coated with a mesoporous oxide 56. Potassium ions 58, for example, are in contact with a first side of the cellular membrane 52. When a laser 40 excites or energizes the biosensor 50, the laser provides an electrochemical gradient that can drive the potassium ions 58 through the ion channels 60 in the cellular membrane 52.

Figure 6:
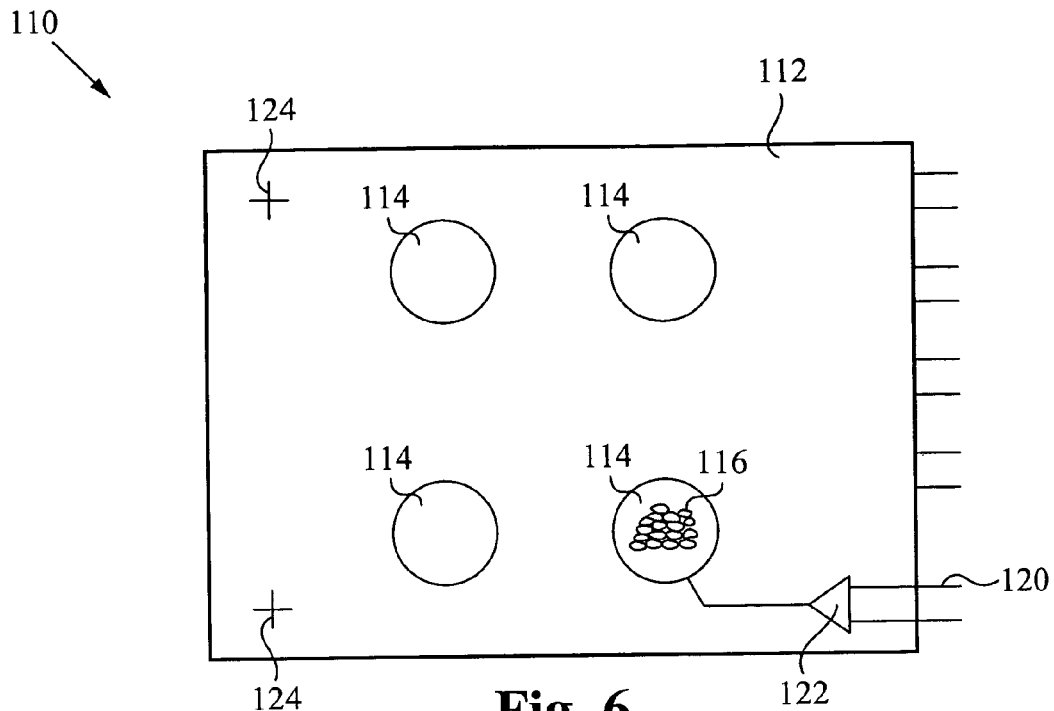
FIG. 6 shows a semiconductor chip incorporating membrane carrier sites for patch clamp analysis according to another example form of the present invention.

FIG. 6 shows another example system 110 for carrying out a method of patch clamp analysis according to the present invention. In this embodiment, an electronic chip 112 preferably includes one or more portions or islands 114 of porous semiconductor material, upon which one or more cells forming a cellular membrane 116 can be grown or deposited. Each island 114 is preferably functionally similar in construction and operation to the system described above with reference to FIG. 1. Circuitry integrated into the chip 112 preferably conducts signals from integrated electrodes maintained in electrically conductive communication with the cell ion channels to one or more pins 120 extending from the chip, for connection to an external computer or other apparatus for receiving, processing, displaying and/or recording patch clamp results.

Figure 7:
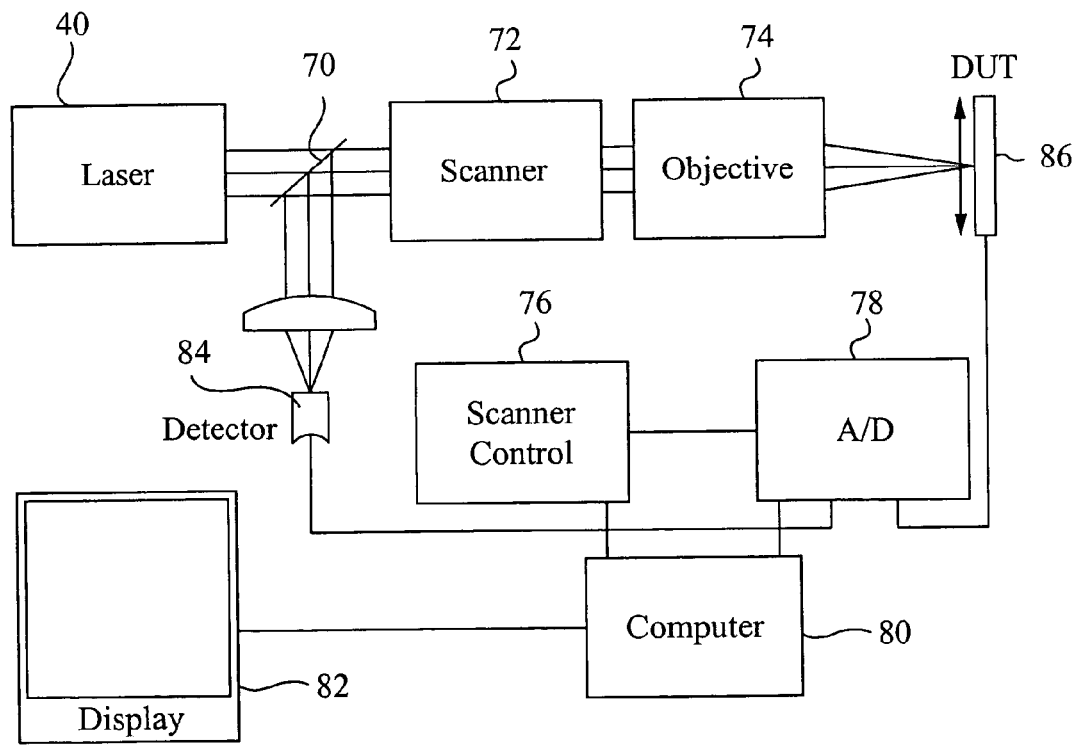
FIG. 7 shows an automated system for controlling laser scanning across cellular membranes, according to an example embodiment of the present invention.

The chip optionally incorporates onboard voltage clamp circuitry, and/or one or more onboard amplifiers 122 to amplify the signals from the ion channel electrodes. In further embodiments of the invention, disposable wafers or substrate sections are provided for supporting a cellular membrane to be subject to patch clamp analysis, which wafers are replaceably coupled to a reusable chip, in place of the islands 114 described above. The chip 112 optionally also includes one or more positional indicators 124, whereby an optical reader or scanner can identify the presence of the chip and locate the islands or substrate sections for automated laser scanning. In further embodiments, the invention further comprises an automated system, such as shown in FIG. 7 for example, for controlling laser scanning across the cellular membranes. Precise software-implemented positional control and analysis are preferably provided in combination with the automated control system.

FIG. 7 shows an automated system for controlling laser scanning across cellular membranes, according to an example embodiment of the present invention. The laser 40 projects a beam to a beam splitter 70 which splits the light to a scanner 72 and a detector 84. After the light is scanned, it goes to an objective 74 which focuses the beam on a Device Under Test (DUT) 86. Then an analog/digital (A/D) converter 78 coverts the analog signal received from the DUT 86 to a digital signal which then goes to a scanner control unit 76 and a computer 80. The scanner control unit 76 also sends data to the computer 80. The detector 84 also sends data to the A/D converter 78 which is converted and sent to the computer 80. After the computer 80 analyzes the data received from the A/D converter 78 and the scanner control unit 76, the data is displayed on a display 82.

In an alternative embodiment, a system and method of patch clamp analysis uses a solid electrolyte polymer. A cellular membrane is preferably deposited on a porous semiconductor substrate, such as a silicon wafer. A solid electrolyte conductive polymer, which fills a reservoir, is preferably applied to a first or lower side of the wafer such that the solid electrolyte polymer is in contact with the lower part of the cellular membrane. The solid electrolyte polymer can be at least one of a gelatin, starch, acacia gum, or a polymer blend that includes at least one or more ions. The ions can be potassium, chloride and sodium. An electrolytic solution is preferably applied over the membrane. A plurality of nano- or micro-scale channels or pores preferably extend through the substrate, into communication with the cell membrane of individual cells of the cellular membrane. Suction is applied to the cell membranes through the pores to ensure a seal is formed around the pores, and optionally to break the cell membrane and provide electrically conductive communication between the cell interior and the electrolytic fluid in the pore. Suction is preferably applied by applying a negative pressure from the first or lower side of the semiconductor substrate through pores.

One or more first electrodes are preferably provided in electrically conductive communication with the electrolytic solution on a first side of the membrane, and one or more second electrodes are preferably provided in electrically conductive communication with the cell interior or second side of the membrane; and the voltage is clamped between the first and second electrodes such that the voltage is maintained constant at any new level and current can be measured.

Two different types of fixturing structures are included to assist in testing and characterizing the patch clamp chips. The first type of fixturing is a glass reservoir in which the chip is attached along with other plumbing to allow electrical and fluid connections to the back of the chip. The structure is suited better for placing whole cells on the surface of the chip for characterization. The second type of fixturing is a glass block in which holes were drilled to allow access to the back of the chip and to allow a standard patch-clamp pipette to be attached to the block. The structure is very small and allows electrical and fluid access to the back of the tips. The standard pipette port allows normal and readily available tooling to be used for interfacing to the structure. The structure is better suited for laminating thin membranes onto the surface of the substrate.

The method and system of the present invention improve membrane stability and accommodate changes in temperature and volume on the reservoir.

The system and method of the present invention are adaptable for use in connection with a number of applications to monitor electrical activity in various biological tissues. For example, in cancer research, it is often desirable to monitor calcium levels in cancer cells and compare those levels with the calcium levels in healthy cells. The system and method of the present invention can be applied to such research to track calcium ion concentration and transport.

The system and method of the present invention are also adaptable to neuroscience applications, for example wherein multiple neurons are subjected to analysis, and the effect on downstream neurons, resulting from stimulation of a target upstream neuron, can be observed.

In another application, olfactory neurons disposed on a semiconductor substrate can form a biosensor to be used as an "artificial nose," for example for use in detection of explosives or drugs. By monitoring the electrical activity of the olfactory neurons upon exposure to sampled substance, various target substances can be identified or their absence can be confirmed.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A method of patch clamp analysis of one or more biological cellular membranes, the method comprising:
   a. applying one or more cells comprising the one or more biological cellular membranes to a semiconductive substrate having at least one channel extending therethrough;
   b. applying a solid electrolyte to a lower part of the semiconductive substrate and at least one of the biological cellular membranes such that the solid electrolyte is in contact with a lower part of the at least one of the cellular membranes to conductively contact at least one of the one or more biological cellular membranes;
   c. placing a first electrode in conductive contact with a first side of at least one of the one or more biological cellular membranes, and a second electrode in conductive contact with a second side of the at least one of the one or more biological cellular membranes;
   d. scanning a laser beam cell by cell across the one or more biological cellular membranes, wherein the laser beam triggers the opening or closing of an ion channel of at least one of the one or more biological cellular membranes; and
   e. detecting a current between the first electrode and the second electrode.

2. The method of claim 1, wherein detecting a current between the first electrode and the second electrode comprises measuring ion current to detect activity of the ion channel through at least one of the one or more biological cellular membranes.

3. The method of claim 1, further comprising clamping the voltage between the first electrode and the second electrode.

4. The method of claim 1, wherein the laser generates photo-electric effect to activate the ion channel of at least one of the one or more biological cellular membranes.

5. The method of claim 1, wherein the laser generates photo-induced electron imbalance resulting in an electric current through the ion channel of at least one of the one or more biological cellular membranes.

6. The method of claim 1, wherein the laser generates photo-induced electrochemical gradient driving ions through the ion channel of at least one of the one or more biological cellular membranes.

7. A method of patch clamp analysis of one or more cellular membranes, the method comprising:
   a. depositing one or more cells comprising the one or more cellular membranes on a semiconductive substrate having at least one channel extending therethrough;
   b. applying a solid electrolyte to the semiconductive substrate to conductively contact at least one of the one or more cellular membranes;
   c. applying an electrolytic solution over at least one of the one or more cellular membranes;
   d. applying suction through one or more pores to at least one of the one or more cellular membranes to ensure a seal is formed around the one or more pores;
   e. placing a first electrode in conductive contact with a first side of at least one of the one or more cellular membranes, and a second electrode in conductive contact with a second side of at least one of the one or more cellular membranes;
   f. scanning a laser beam cell by cell across the one or more cellular membranes, wherein the laser beam triggers the opening or closing of an ion channel of at least one of the one or more biological cellular membranes; and g. detecting a current between the first electrode and the second electrode.

8. The method of claim 7, wherein applying suction to at least one of the one or more cellular membranes to ensure a seal is formed further comprises breaking at least one of the cellular membranes and providing electrically conductive communication between the cell interior and the electrolytic solution.

9. The method of claim 7, wherein the solid electrolyte is a composition made from biopolymer and at least one of K, Na, and Cl ions.

10. The method of claim 7, wherein the electrolytic solution includes about 125 mM NaCl, about 5 mM KCl, about 1.25 mM $NaH_2PO_4$ and about 5 mM Tris (pH 7.4).

11. The method of claim 7, wherein detecting a current between the first electrode and the second electrode comprises measuring ion current to detect activity of the ion channel through at least one of the one or more cellular membranes.

12. The method of claim 7, further comprising clamping the voltage between the first electrode and the second electrode.

* * * * *